United States Patent
Penka

(10) Patent No.: US 11,694,657 B2
(45) Date of Patent: Jul. 4, 2023

(54) HEART LUNG MACHINE HAVING CONTROL ASSEMBLY WITH SPACE-SAVING DISPLAY FEATURES

(71) Applicant: LivaNova Deutschland GmbH, Munich (DE)

(72) Inventor: Ottmar Penka, Munich (DE)

(73) Assignee: LivaNova Deutschland GmbH

( * ) Notice: Subject to any disclaimer, the term of this patent is extended or adjusted under 35 U.S.C. 154(b) by 0 days.

(21) Appl. No.: 17/316,002

(22) Filed: May 10, 2021

(65) Prior Publication Data
US 2021/0264880 A1    Aug. 26, 2021

Related U.S. Application Data

(63) Continuation of application No. PCT/EP2018/086323, filed on Dec. 20, 2018.

(51) Int. Cl.
*G09G 5/30* (2006.01)
*G16H 40/63* (2018.01)
*G09G 5/24* (2006.01)

(52) U.S. Cl.
CPC ............ *G09G 5/30* (2013.01); *G09G 5/24* (2013.01); *G16H 40/63* (2018.01); *G09G 2340/12* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 8,696,587 B1* | 4/2014 | Whitfield | A61B 7/04 600/528 |
| 2011/0193704 A1* | 8/2011 | Harper | A61B 5/14 340/573.1 |
| 2012/0204875 A1 | 8/2012 | Brazy et al. | |
| 2013/0066612 A1* | 3/2013 | Russell | G05B 19/05 703/7 |
| 2015/0272487 A1* | 10/2015 | Ranucci | A61B 5/6866 600/301 |

(Continued)

FOREIGN PATENT DOCUMENTS

WO    2016180853 A1    11/2016

OTHER PUBLICATIONS

Author: dreamcometrue_2016; Title: Just released my iOS Heart Rate Monitor App; Date: Nov. 30, 2018; Source: https://www.reddit.com/r/iphone/comments/a1qkpa/just_released_my_ios_heart_rate_monitor_app/ (Year: 2018).*

(Continued)

*Primary Examiner* — Jwalant Amin
(74) *Attorney, Agent, or Firm* — Seager, Tufte & Wickhem LLP.

(57) ABSTRACT

Embodiments of the subject matter include a heart lung machine (HLM), including a plurality of actuators and a peripheral processing unit configured to receive a set of parameter data from the plurality of actuators. The HLM also may include a peripheral display device configured to present a subset of the set of parameter data and a control assembly comprising a control display device configured to present a user interface having a representation of a parameter value and an associated indication, where at least a portion of the associated indication overlaps at least a portion of the representation of the parameter value.

20 Claims, 8 Drawing Sheets

(56) References Cited

U.S. PATENT DOCUMENTS

| | | | |
|---|---|---|---|
| 2017/0255614 A1* | 9/2017 | Vukosavljevic | ........ G06F 40/58 |
| 2018/0042578 A1* | 2/2018 | Anand | ................... A61B 8/465 |
| 2018/0099109 A1 | 4/2018 | Kinsky et al. | |
| 2018/0204361 A1* | 7/2018 | Tinsman | ................. G06T 11/60 |
| 2018/0289886 A1* | 10/2018 | Hyde | ................. A61M 60/546 |

OTHER PUBLICATIONS

International Search Report for International Application No. PCT/EP2018/086323 dated Aug. 28, 2019.
Written Opinion for International Search Report PCT/EP2018/086323 dated Aug. 28, 2019.

\* cited by examiner

HEART LUNG MACHINE HAVING CONTROL ASSEMBLY WITH SPACE-SAVING DISPLAY FEATURES

CROSS REFERENCE TO RELATED APPLICATIONS

This application is a continuation of International Application No. PCT/EP2018/086323, filed Dec. 20, 2018, the disclosure of which is incorporated herein by reference.

TECHNICAL FIELD

The present disclosure relates to a display arrangement for medical equipment, in particular, for heart lung machines.

BACKGROUND

Heart lung machines often have display devices that are not located near a perfusionist or other clinician. Similarly, in many heart lung machines, controls for individual components are connected directly to those components, which are distributed across various parts of the machine. As the user of the HLM's focus generally is on the oxygenator and venous reservoir, which may be configured to be disposed on one end of the HLM, the user may have to move to see the peripheral display unit and/or operate control devices corresponding to other components, thereby distracting the user's attention from the oxygenator and venous reservoir.

SUMMARY

Embodiments of the subject matter disclosed herein include a heart lung machine (HLM), including a plurality of actuators and a peripheral processing unit configured to receive a set of parameter data from the plurality of actuators. In embodiments, the HLM includes a peripheral display device configured to present a subset of the set of parameter data. The HLM also may include a plurality of actuator control units (ACUs), where each of the plurality of ACUs is operably connected to one of the plurality of actuators; and a control assembly comprising a control display device configured to present a user interface having a representation of a parameter value and an associated indication, where at least a portion of the associated indication overlaps at least a portion of the representation of the parameter value.

Embodiments may include one or more computer-readable media having embodied thereon computer-executable instructions that, when executed by a processing unit, cause the processing unit to facilitate presenting a user interface on a control display device of a heart lung machine. The user interface may include a representation of a parameter value and an associated indication, where at least a portion of the associated indication overlaps at least a portion of the representation of the parameter value.

Embodiments of the subject matter disclosed herein may further include a method of presenting a user interface on a control display device of a heart lung machine (HLM), the HLM including a plurality of actuators and a peripheral processing unit configured to receive a set of parameter data from the plurality of actuators. The HLM may include a peripheral display device configured to present a subset of the set of parameter data and a control assembly comprising the control display device. In embodiments, the method may include presenting a representation of a parameter value and presenting an associated indication, where at least a portion of the associated indication overlaps at least a portion of the representation of the parameter value.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
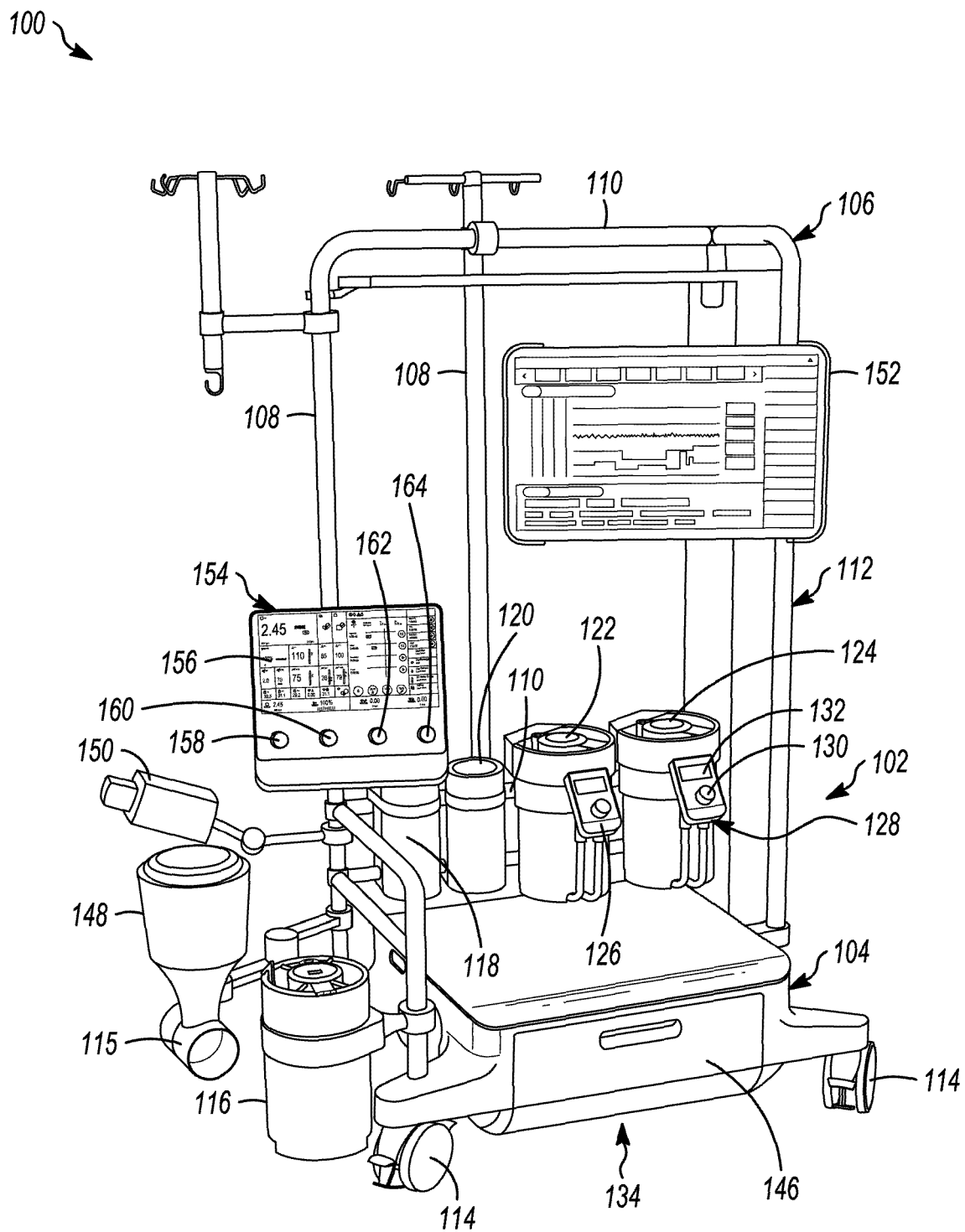
FIG. 1A is a front perspective view of an illustrative heart lung machine (HLM), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values—e.g., terms of magnitude, measurement, and/or other degrees of qualitative and/or quantitative observations that are used herein with respect to characteristics (e.g., dimensions, measurements, attributes, components, etc.)—and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments of the subject matter disclosed herein include aspects of heart lung machines (HLMs) that include a control assembly configured to be disposed near an oxygenator and venous filter and having a control display device. The control display device may be smaller than a central display device to facilitate positioning it near the user's position and reduce obstruction of the user's view of the oxygenator and/or venous reservoir, which generally are the objects of the user's focus during an operation.

Providing a smaller control display device may be challenging due to the limited screen space and the typical method of displaying measurement units includes displaying them to the right of the representation of the parameter value. As the units have different lengths (e.g. "mmHg" is longer than, say, "l" for liter or "° C."). When configuring such a control device, the space for the measurement units of each value field must be foreseen for the longest unit in the system, and, as the display screens are to some extent configurable (at one location there can be a long unit or a short unit), this stage may include a number. To facilitate using a smaller display device, the contents of the user interface may be compressed to save display space by presenting the representation of the parameter value and an indication of the measurement units in the same location, one at least partially overlapping the other.

Figure 1B:
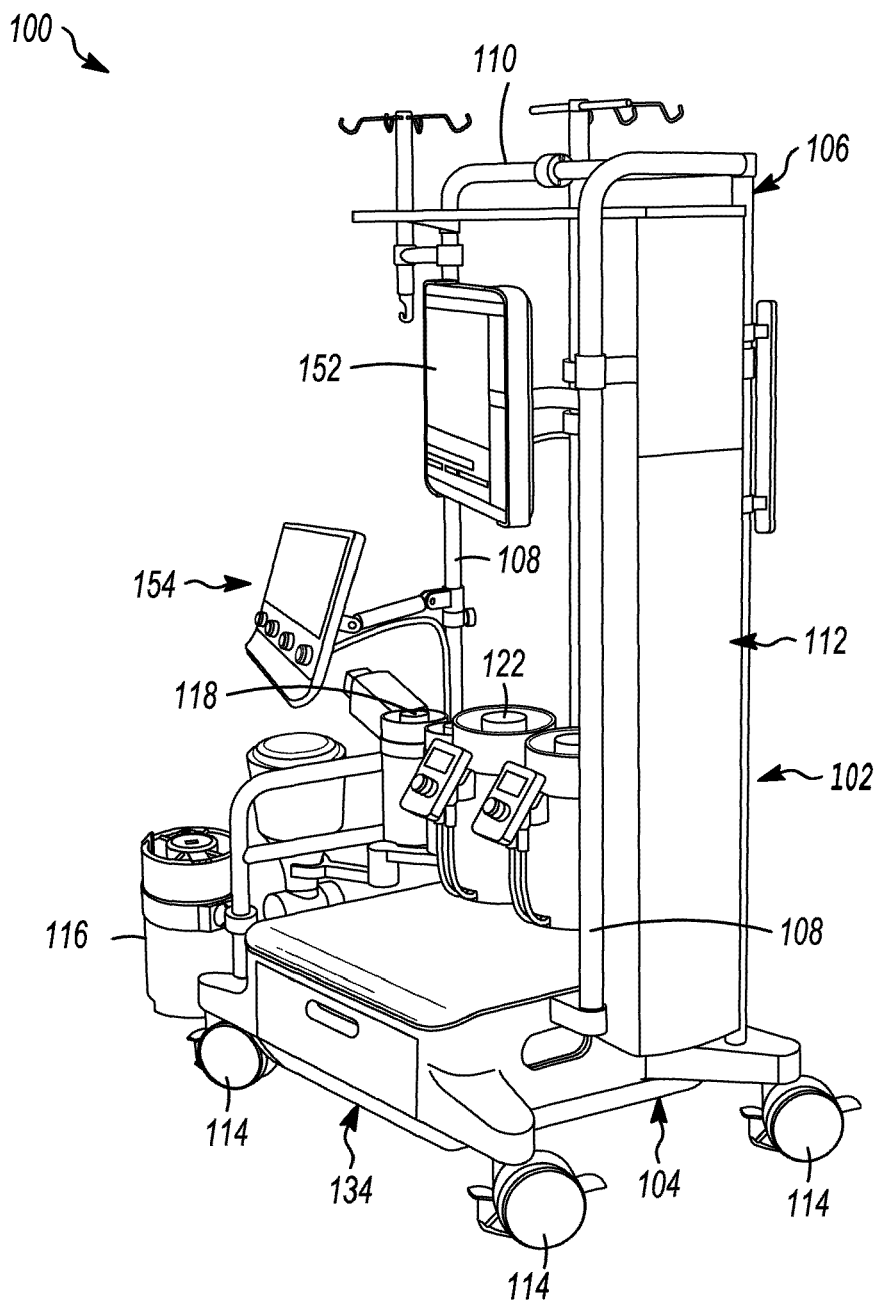
FIG. 1B is a side perspective view of the illustrative HLM depicted in FIG. 1A, in accordance with embodiments of the subject matter disclosed herein.

FIG. 1A is a front perspective view of an illustrative heart lung machine (HLM) 100, in accordance with embodiments of the subject matter disclosed herein; and FIG. 1B is a side perspective view of the illustrative HLM 100 depicted in FIG. 1A, in accordance with embodiments of the subject matter disclosed herein. As shown, the HLM 100 includes a trolley 102 having a base 104 that includes an internal cavity (not shown) for housing any number of different controls, electrical circuits, hydraulic circuits, a battery discharger, and/or the like. For example, in embodiments, a peripheral processing unit may be disposed within the base 104. A mast assembly 106 is coupled to the base 104 and extends upwards from the base 104. The mast assembly 106 may include any number of different mast components, including vertical poles 108, horizontal rails 110, and/or the like. In embodiments, the trolley 102 includes an enclosure 112 that is configured to facilitate cable management, provide A/C outlets, include a power switch for the HLM 100, include an extension box, and/or the like. As shown, the trolley 102 also may include wheels 114 coupled to the base 104.

As shown, the HLM 100 also may include a number of different types of components such as an oxygenator 115 (which may actually be considered to be an element of an extracorporeal circuit used with the HLM, but may be referred to herein as being a component of the HLM due to being connected to the trolley 102); pumps 116, 118, 120, 122, 124; and/or the like. In embodiments, one or more of the components 115, 116, 118, 120, 122, and 124 (and/or others) may be coupled to any number of different portions of the mast assembly 106, and may include, for example, an exposed actuator control unit (ACU). For example, as shown, pumps 122 and 124 may each include an exposed ACU 126 and 128, operably connected thereto, respectively. As shown, an ACU 128 may include a control knob 130 configured to receive user input (e.g., manipulation of the knob 130) for controlling operation of the pump 124, and an information display device 132 configured to present information associated with the pump such as, for example, one or more parameters (e.g., measured device parameters such as, for instance, flow, rpm, etc.). According to embodiments, an ACU may be configured to facilitate control of a pump, a motorized clamp, a motorized occluder, an infusion device, and/or any number of other types of devices that may be associated with an HLM.

Traditionally, HLMs have utilized roller pumps that are each integrated into a modular console component. The modular console components are stacked next to one another on the base of an HLM to provide an array of pumps. The modular console component also houses an ACU having an interface for controlling the corresponding integrated roller pump. One advantage of having the ACU interface provided at the modular console component is that, during an emergency situation, the perfusionist can easily determine the ACU that corresponds to a particular roller pump. More recently, mast mounted roller pumps (without the modular console component housing) have been utilized in HLMs. Mast mounted pumps provide more flexibility in the configuration of the HLM; however, if the ACUs for the mast mounted pumps are located remotely, or detached from, the mast mounted pumps, it's potentially more difficult for the perfusionist to identify the ACU that controls a particular pump.

Embodiments of the present disclosure include mast mounted roller pumps, such as pumps 122 and 124 of FIG. 1A, having corresponding ACUs, such as ACUs 126 and 128, respectively. The ACUs 126 and 128 are attached, connected, or otherwise operatively coupled to the corresponding mast mounted roller pumps 122 and 124. The connectedness, or close proximity of the ACU to the mast mounted roller pump allows the user to precisely determine the ACU that controls a particular mast mounted roller pump in a high pressure, or emergency situation, including a situation where the control display device 156 is not functioning properly or is disabled. Thus, the ability to mount the pumps 122 and 124 to the mast assembly 106 allows a much wider range of configurations to meet the user's particular needs.

Figure 1C:
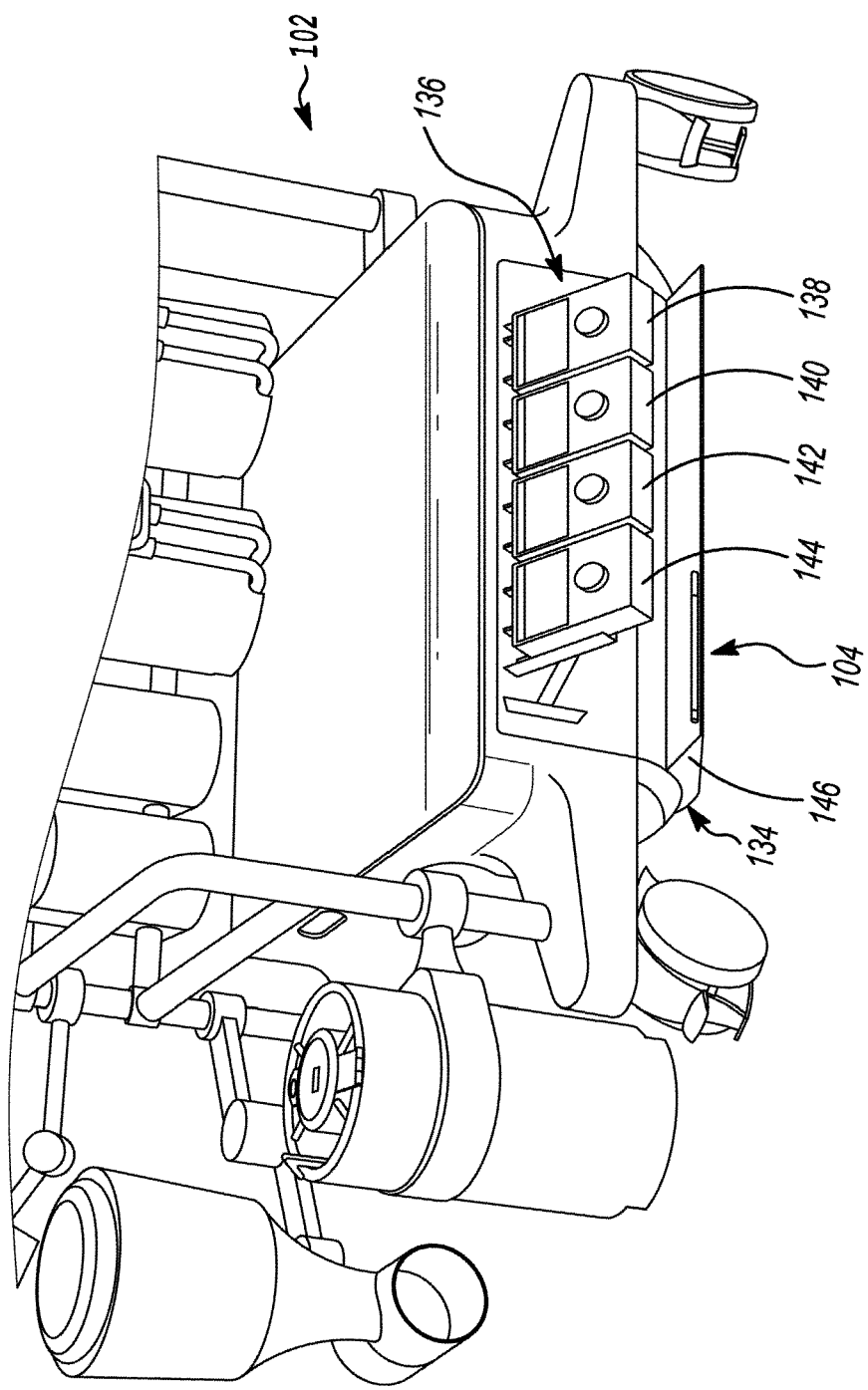
FIG. 1C is a partial perspective view of the base of the trolley depicted in FIGS. 1A and 1B, in accordance with embodiments of the subject matter disclosed herein.

FIG. 1C is a partial perspective view of the base 104 of the trolley 102 depicted in FIGS. 1A and 1B, in accordance with embodiments of the subject matter disclosed herein. As shown in FIG. 1C, the base 104 of the trolley 102 may include a lower housing 134 having an enclosure 136 configured to house one or more ACUs 138, 140, 142, and 144. In embodiments, any number of ACUs may be disposed in the enclosure 136. For example, in embodiments, all of the ACUs for actuators associated with the HLM 100 may be disposed at least partly in the enclosure 136. In embodiments, one or more ACUs may be exposed by being disposed directly on or near the corresponding actuators. According to embodiments, the enclosure 136 may be configured to be closed to protect the ACUs disposed therein, or opened to reveal the ACUs. For example, the lower housing 134 may include a drawer, cabinet, and/or the like. As shown, in embodiments, the lower housing 134 may include a door 146 configured to be opened and closed to selectively expose or conceal the enclosure 136. Each of the ACUs 138, 140, 142, and 144 may be operably connected to a corresponding one of the components 116, 118, 120, 122 (e.g., in cases in which the pump 122 does not include an exposed ACU 126), or 124 (e.g., in cases in which the pump 124 does not include an exposed ACU 128) and/or other actuators.

As is further shown in FIGS. 1A and 1B, the HLM 100 may include any number of other components such as, for example, a venous reservoir 148 (which may be, for example, a component of an extracorporeal circuit that may be used in combination with the HLM 100), an electronic venous occluder (EVO) 150, a peripheral display device 152, a control assembly 154, any number of various types of sensors, and/or the like. According to embodiments, any number of the components discussed herein, others not discussed herein, or aspects of the components (e.g., sensors and/or actuators associated with components) may be operably connected to the peripheral processing unit (not shown), which may be configured to receive parameter data from any one or more of the components, process parameter data, receive control signals from any one or more input devices (e.g., ACU control knobs 130, etc.), provide control signals to any one or more of the components, and/or the like.

In embodiments, the peripheral display device 152 may be operably connected to the peripheral processing unit and configured to present a set of parameter data received from the peripheral processing unit. In embodiments, the peripheral display device 152 may be, include, or be included within a data recording and/or management system. That is, for example, the peripheral display device 152 may include, or be otherwise associated with, a processing unit separate from that of the HLM, and/or may be configured to record and/or display any number of different operative HLM parameters. In some implementations, for example, the peripheral display device 152 may be configured to obtain and record all of the operative HLM parameter values and/or patient parameters provided by any number of additional monitoring devices. The peripheral display device 152 may be configured to present, graphically, representations of any number of the obtained parameter values, changes in parameter values over time, derived parameter values (e.g., values derived from parameter values), and/or the like.

During an operation, the primary focus of a user of the HLM 100 generally is the oxygenator 115 and the venous reservoir 148. Accordingly, embodiments of the subject matter disclosed herein provide a control assembly 154 near those two components 115 and 148 so that the user can access control devices and view displayed parameters without having to move away from, or be distracted from, the oxygenator 115 and venous reservoir 148. According to embodiments, the control assembly 154 may include a control display device 156 and a number of input control devices 158, 160, 162, and 164. In embodiments, the control assembly 154 may include any number of input control devices (e.g., 1, 2, 3, 4, 5, 6, etc.) and the number of input control devices may be less than or equal to the number of ACUs in the enclosure 136. The control display device 156 may be configured to present a subset of the parameters presented by the peripheral display device 152 and/or the peripheral display device 152 may be configured to present a subset of the subset of parameters presented by the control display device 156. A different subset of the set of parameter data may be displayed by the peripheral display device 152. In embodiments, the peripheral display device 152 may be configured to display real-time waveform traces, while the control display device 156 may be configured to display numerical representations of the same and/or different parameters.

That is, for example, regardless of what is displayed on the peripheral display device 152, the control display device 156 may be configured to display a specified subset of parameter data that is particularly useful and/or important with respect to a procedure being performed. That specified subset of parameter data may be predetermined, based on the type of procedure; dynamically presented, based on a status of the patient and/or device; and/or the like. In embodiments, all of the information configured to be presented on the control display device 156 may be presented simultaneously—that is, without having tabs for accessing screens showing additional information, without requiring menus for accessing screens showing additional information during a procedure, and/or the like. In embodiments, the control display device 156 may include selectable representations presented onscreen that can be used to configure the display such as, for example, by enabling a user to select a display mode corresponding to a particular HLM component (e.g., a centrifugal pump, a roller pump, etc.), to select a particular display module (e.g., a pre-configured set of data fields in a particular arrangement), and/or the like.

According to embodiments, the peripheral display device 152 and/or the control display device 156 may include an input mechanism configured to enable user interaction with one or more features displayed on the display device 152 and/or 156. That is, for example, the peripheral display device 152 and/or the control display device 156 may be, or include, a touchscreen device configured to receive user input. In embodiments, the peripheral display device 152 and/or the control display device 156 may include an input device connected thereto such as, for example, a mouse, a trackpad, a joystick, and/or the like.

According to embodiments, for example, additional data from devices external to the HLM (e.g., blood gas monitors, electrocardiographs, ventilators, patient monitors, etc.) may be displayed on the peripheral display device 152. As indicated above, the peripheral display device 152 may be controlled by a peripheral processing unit that is separate from the central system unit, the control display device or any other central unit of the HLM. The peripheral processing unit associated with the peripheral display device 152 may be configured to obtain parameter values (e.g., from the central system unit, sensors, actuators, external devices, etc.) and may be configured to collect the data in a database. The peripheral processing unit may be communicatively coupled to the peripheral display device 152, HLM components, and/or external devices. In embodiments, while the peripheral processing unit may be configured to receive data from the central system unit, an interface unit or any other communication port embedded in the HLM, the peripheral processing unit may be configured so as to not send any data to the central system unit, to the interface unit or other communication ports of the HLM. In other embodiments, the peripheral processing unit and the central system unit, the interface unit or any other communication port of the HLM may be configured to exchange data with one another and/or other devices.

According to embodiments, a user may select which data is to be stored by which processing or system unit.

The peripheral processing unit associated with the peripheral display device may be configured to allow user interaction therewith, generate reports based on the obtained data, generate printable documents corresponding to a medical procedure, interact with a printer to cause the printer to print such reports, and/or the like. In embodiments, the peripheral processing unit may be configured to generate, and cause the peripheral display device to present, graphs (e.g., trend charts, curves, etc.) and/or other visual representations of any number of various aspects of data received from HLM components and/or external devices. In embodiments the peripheral display device may be configurable such that a user can select certain types of data and/or representations thereof to display, the manner in which it is displayed, and/or the like. In contrast, for example, the control display device 156 may include only limited configurability, if at all. In this manner, the control display device 156 can be relied upon to present representations of data relevant to the HLM's current use. According to other embodiments, the control display device 156 may have any amount of configurability.

In embodiments, each of the input control devices 158, 160, 162, and 164 may be operably connected to one of the actuators and may be configured to receive user input for controlling an operation of the actuator. According to embodiments, the input control devices 158, 160, 162, and 164 may be operably connected to the respective ACUs 138, 140, 142, and 144, in which case, the input control devices 158, 160, 162, and 164 act in parallel to the ACUs, but do not have priority over them in controlling the actuators. In embodiments, the input control devices are directly connected to the respective ACUs, and the ACUs are connected to the respective actuators, such that an actuator can be controlled by an input control device only through an ACU or directly by an ACU. Therefore, the ACU has prevalence over the input control device in controlling the actuator.

The illustrative HLM 100 shown in FIGS. 1A-1C is not intended to suggest any limitation as to the scope of use or functionality of embodiments of the present disclosure. The illustrative HLM 100 also should not be interpreted as having any dependency or requirement related to any single component or combination of components illustrated therein. Additionally, various components depicted in FIGS. 1A-1C may be, in embodiments, integrated with various ones of the other components depicted therein (and/or components not illustrated), all of which are considered to be within the ambit of the present disclosure.

Figure 2A:
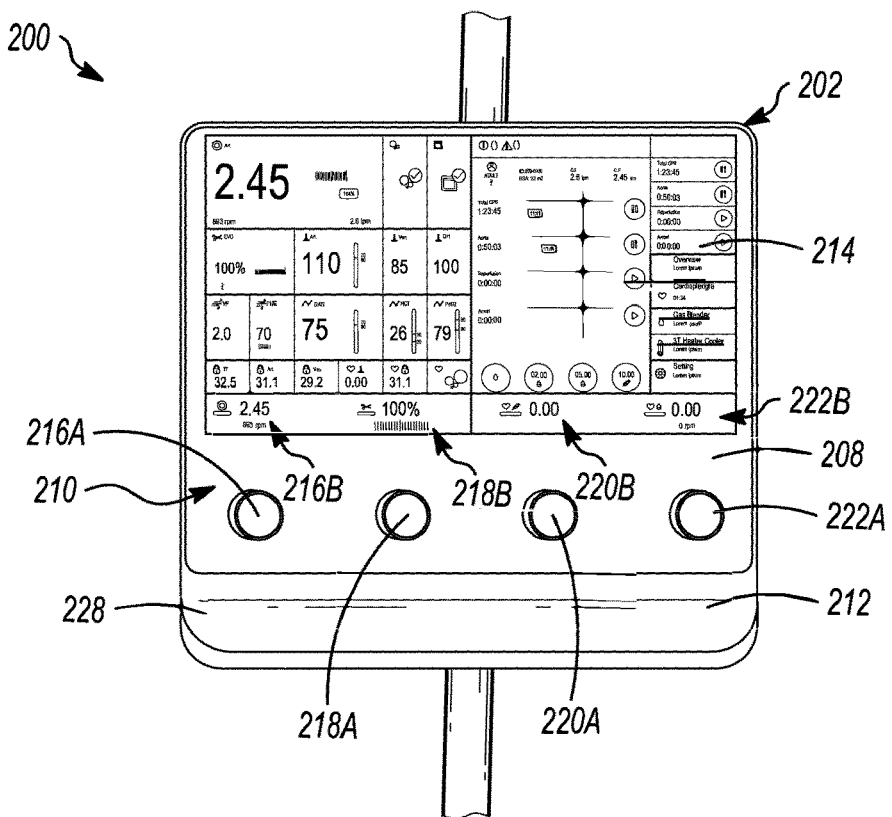
FIG. 2A is a front perspective view of an illustrative control assembly, in accordance with embodiments of the subject matter disclosed herein.
Figure 2B:
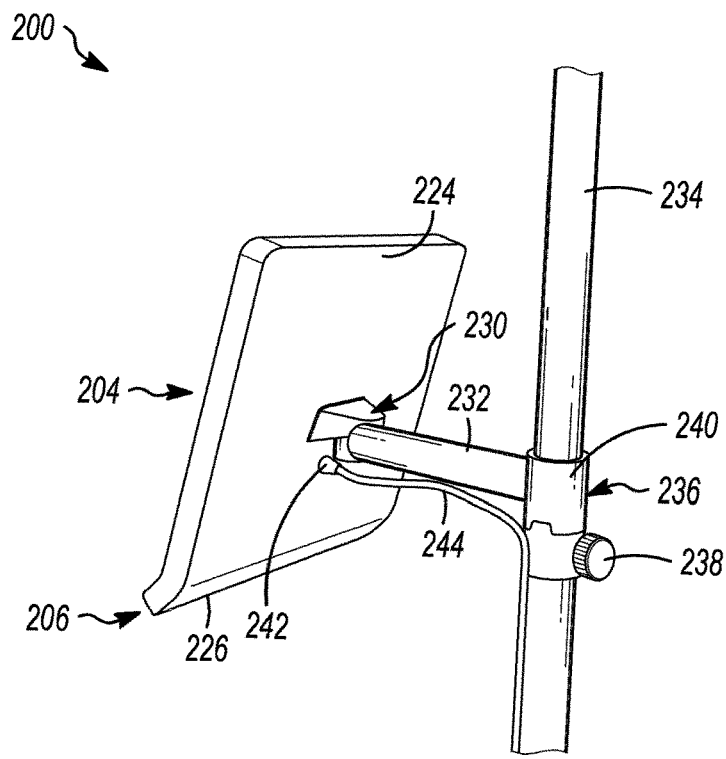
FIG. 2B is a rear perspective view of the illustrative control assembly depicted in FIG. 2A, in accordance with embodiments of the subject matter disclosed herein.

FIG. 2A is a front perspective view of an illustrative control assembly 200 of an HLM, in accordance with embodiments of the subject matter disclosed herein; and FIG. 2B is a rear perspective view of the illustrative control assembly 200 depicted in FIG. 2A, in accordance with embodiments of the subject matter disclosed herein. According to embodiments, the illustrative control assembly 200 may be, be similar to, include, or be included within the control assembly 154 depicted in FIGS. 1A-1B. In embodiments, the control assembly 200 may be configured to provide a graphical user interface (GUI) that facilitates enabling a user to control, configure, access, and/or otherwise interact with components of the HLM and/or external components interfaced with the HLM. For example, the GUI may facilitate configuring HLM components, monitoring values from actuators and/or sensors, setting timers and/or reminders, and/or the like. The control assembly 200 may provide visual and/or audible notifications, alarms, and/or the like.

As shown in FIGS. 2A-2B, for example, the illustrative control assembly 200 includes a body 202 having a first portion 204 that is at least approximately rectangular and a second portion 206 that extends away from a front surface 208 of the first portion 204. According to embodiments, the first and second portions 204 and 206 of the body 202 may be integrated, removeably coupled together, permanently coupled together, and/or the like. In embodiments, as shown, the body 202 may include a solid piece, with a control panel insert 210 configured to be disposed within a cavity (not shown) defined in a front surface 212 of the body 202. The control panel insert 210 may include a display device 214 and a number of input control devices 216A, 218A, 220A, and 222A. In embodiments, the display device 214 may be, or include, a touchscreen device configured to receive user input via touch (e.g., by a user's finger, a stylus, and/or the like).

Each of the input control devices 216A, 218A, 220A, and 222A may be configured to be assigned to an actuator on the HLM such as, for example, a small roller pump drive, a large roller pump drive, a centrifugal pump drive, an electronic venous line occluder (EVO), and/or the like. Each of the input control devices 216A, 218A, 220A, and 222A may include a rotatable knob that can be used to adjust an adjustable operating parameter of the corresponding actuator. In embodiments, one or more of the knobs may be configured to be pushed in and/or pulled out to allow further control of additional parameters. In embodiments, one or more of the knobs may be configured to be pushed to toggle through control options, assigned control options by other devices, and/or the like. The control assembly 200 further includes a display region 216B, 218B, 220B, and 222B corresponding to, and disposed adjacent to, each input control device 216A, 218A, 220A, and 222A.

According to embodiments, the display region corresponding to an input control device may be configured to display a parameter value associated with the corresponding actuator. That is, in embodiments, for example, each display region 216B, 218B, 220B, and 222B may be displayed above its corresponding input control device 216A, 218A, 220A, and 222A and may be configured to display a value of the parameter adjustable using the input control device 216A, 218A, 220A, and 222A (e.g., a pump speed in revolutions or rotations per minute (rpm), a pump flow rate in liters per minute (lpm), an occlusion value, etc.). In embodiments, the display region may replicate a similar display region that may be found on an ACU associated with the actuator. In embodiments, each input control device 216A, 218A, 220A, and 222A may include a color (e.g., a colored ring) that matches a color affixed to the corresponding actuator. That matching color may be also affixed to a corresponding ACU and/or may be represented in the corresponding display region 216B, 218B, 220B, and 222B.

In embodiments, the control assembly 200 may include any number of input control devices (e.g., 1, 2, 3, 4, 5, 6, etc.) and the number of input control devices may be less than or equal to the number of ACUs in an actuator enclosure (e.g., the enclosure 136 depicted in FIG. 1C). In embodiments, display device 214 and input control devices 216A, 218A, 220A, and 222A may be disposed in the front surface of the body 202 individually, using two different inserts (e.g., an insert for the display device 214 and an insert for the input control devices 216A, 218A, 220A, and 222A), and/or according to any number of other designs. Any number of display devices and/or input control devices may be provided in the body 202 of the control assembly 200.

In embodiments, the body 202 may include more than one piece (e.g., a pair of half-shell pieces configured to be joined together to form the body 202). As shown, the body 202 generally includes a rear surface 224 opposite the front surface 212. In embodiments, as shown, the rear surface 224 may also include a curved portion 226 corresponding to a curved portion 228 of the front surface 212. In embodiments, one or more of the curved portions 226 and 228 may be angled instead of, or in addition to, being curved. A combination of curved aspects and angled aspects may be used. In embodiments, the front surface 212 may include a curved portion 228, while the rear surface 224 is flat (e.g., does not include a curved portion 226). The second portion 206 of the body 202 is formed by at least a curved and/or angled portion 228 of the front surface 212. The second portion 206 may be configured to be used as a hand rest upon which a user may rest, for example, the palm of the user's hand while, and/or between, operating input control devices. The second portion 206 may also facilitate protecting the input control devices from accidental manipulation, damage, and/or the like.

As shown in FIG. 2B, the rear surface 224 may include a mast connection interface 230 configured to facilitate coupling the control assembly 200 to a connection arm 232 configured to connect the control assembly 200 to a mast component 234 via a mast connector 236. As shown, the mast connector 236 may include a moveable, locking connector 236 having a locking device 238 (e.g., a locking wheel, a lever, a hand gear, etc.) for securing the mast connector 236 in place on the mast component 234. In embodiments, when the locking device 238 is loosened, the mast connector may be configured to be slideably moved up and down the mast component 234 and/or rotated around the mast component 234. That is, for example, the mast connector 236 may include an interface cylinder 240 configured to be concentrically disposed around the mast component 234. In embodiments, the mast connector 236 may be oriented in any number of different directions to facilitate connecting to other mast components (e.g., horizontally to facilitate connection to a horizontal mast rail).

The connection arm 232 may be pivotably connected to the mast connection interface 230 such that the control assembly 200 can be at least partially rotated in one or more directions with respect to the connection arm 232. For example, in embodiments, the connection arm 232 may include a ball configured to be coupled to a socket in the mast connection interface 230 to facilitate pivoting the control assembly 200 in any number of different directions. In other embodiments, the connection arm 232 may be connected by a pin to facilitate rotation in one direction.

As is further shown in FIG. 2B, a connection port 242 disposed in the rear surface 224 may be configured to connect a cable 244 to the control assembly 200. In embodiments, the control assembly 200 may be coupled to a peripheral processing unit and/or a bus of the HLM using only one cable 244. That cable 244 may be configured to transport control signals, parameter data, power, and/or the like. The cable 244 may be, include, or be included within, the bus. For example, the bus may be implemented using circuitry within a central system unit, one or more cables configured to couple the central system unit to one or more different components of the HLM. In embodiments, the cable 244 may be configured to be disposed outside of the connection arm 232 and/or mast component 234, while, in other embodiments, the cable 244 (or at least a portion thereof) may be configured to be disposed within at least a portion of the connection arm 232 and/or at least a portion of the mast component 234.

Figure 2C:
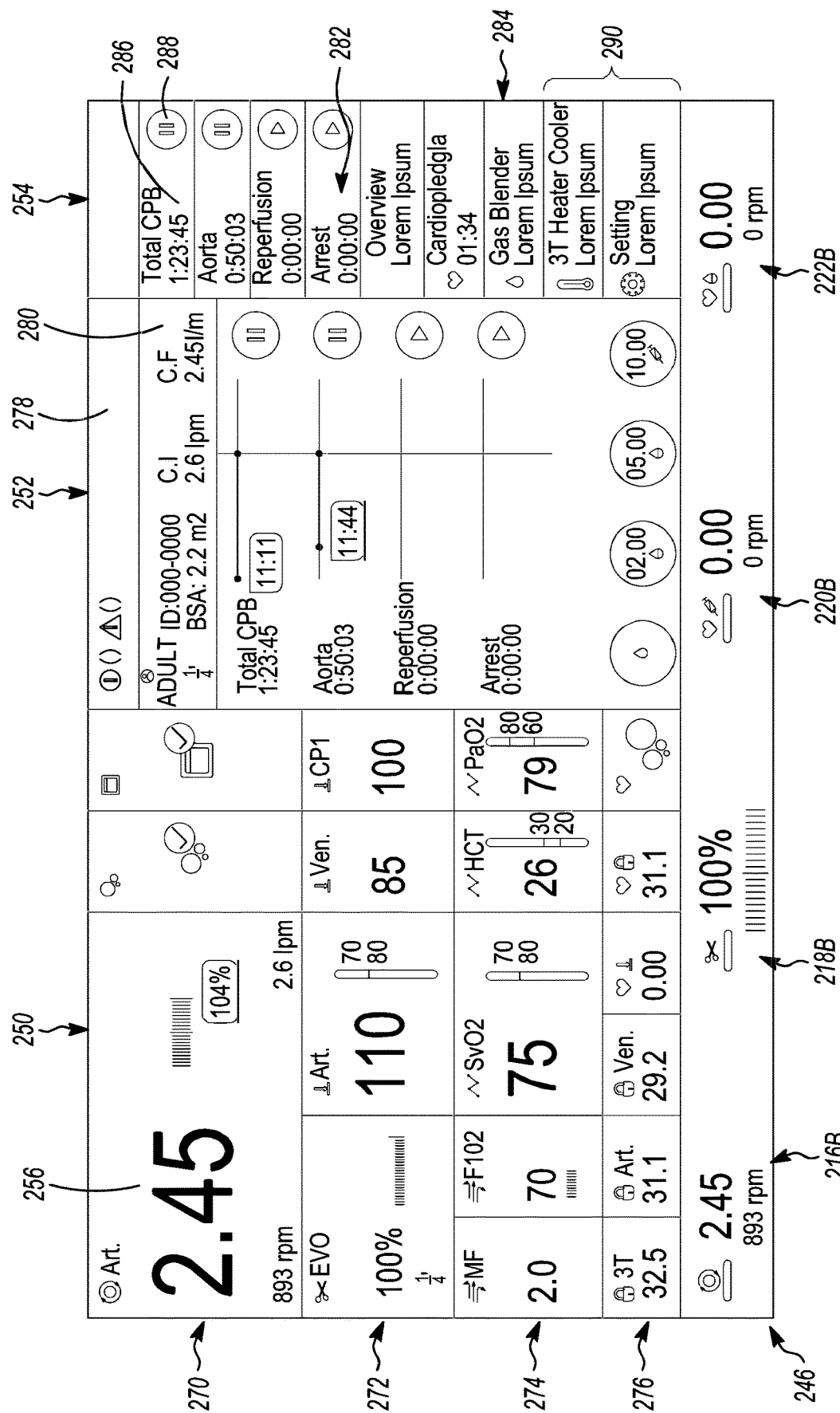
FIG. 2C depicts an illustrative graphical user interface (GUI), in accordance with embodiments of the subject matter disclosed.

According to embodiments, the display device 214 may be configured to present a graphical user interface (GUI) 246, as shown in FIG. 2C. The GUI 246 may include any number of different features and may be configured to facilitate control of one or more HLM components and/or other components, monitoring parameter values, providing notifications and/or alarms, and/or the like. As shown in FIG. 2C, and as mirrored in the conceptual layout 248 depicted in FIG. 2D, the GUI 246 may include a number of presentation areas such as, a monitoring area 250, a dynamic area 252, and a system area 254. According to embodiments, the GUI 246 may include any number of different display areas arranged in accordance with any number of different display schemes. In embodiments, the display areas may be configurable (e.g., selectable, removeable, moveable, etc.), while, in other embodiments, one or more of the display areas may be fixed. That is, for example, in embodiments, the monitoring area 250, the dynamic area 252, and the system area 254 may always be present and may each always occupy the same portion of the GUI 246 so as to facilitate a consistent and predictable user experience, thereby facilitating the efficiency with which a user may utilize the GUI 246.

In embodiments, the monitoring area 250 may be configured to present a number of parameter values obtained from actuators, sensors, and/or other HLM components. According to embodiments, the layout of parameter value display fields may be consistent, while the particular parameters represented may be configurable based on the particular HLM components being used and/or connected in a certain operation. For example, as shown, the monitoring area 250 may include a prominent display field 256 that is configured to present a parameter value corresponding to a parameter of primary interest to a user of the HLM during a particular operation such as, for example, a speed of a pump, or a flow rate, having the most impact on the function of the HLM at that time. The prominent display field 256 may be larger than any other display field in the monitoring area 250 to facilitate its prominence with respect to other aspects of the GUI 246.

Figure 2D:
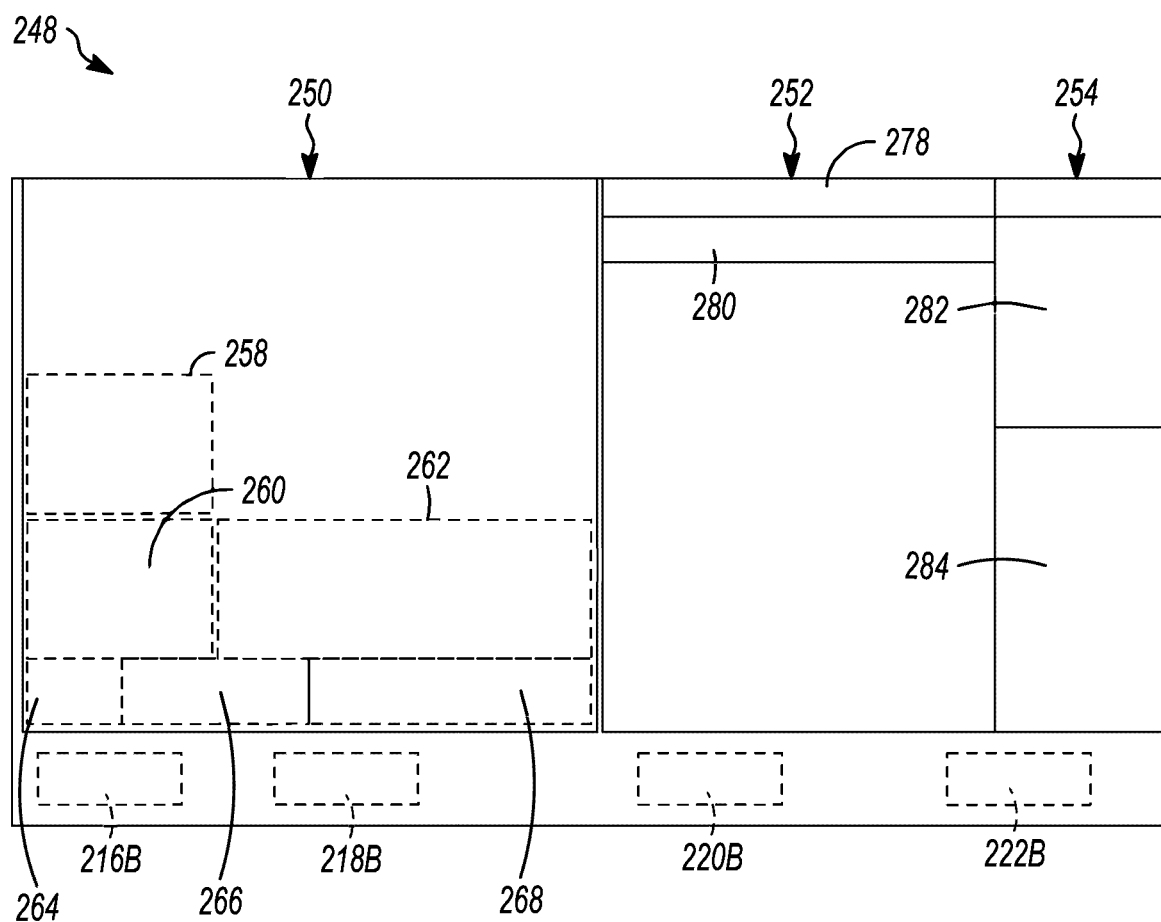
FIG. 2D is a conceptual layout of an illustrative GUI, in accordance with embodiments of the subject matter disclosed.

As illustrated in FIG. 2D, the monitoring area 250 may further include functional display areas 258, 260, 262, 264, 266, and 268. In embodiments, each of the functional display areas 258, 260, 262, 264, 266, and 268 may correspond to a different function performed by the HLM. For example, in embodiments, the functional display areas 258, 260, 262, 264, 266, and 268 may correspond, respectively, to operation of an electronic venous occlude (EVO), gas blending, blood gas monitoring, temperature monitoring, arterial/venous temperature, and cardioplegia. Each functional display area may include one or more display fields configured to present a parameter value associated with the corresponding function. According to embodiments, the monitoring area 250 may include any number of functional display area and/or display fields contained therein. In embodiments, the existence and/or layout of one or more of the functional display fields may be configurable by a user, pre-determined based on related functions being performed, and/or the like. In embodiments, as shown in FIG. 2C, the monitoring area 250 may be organized into rows dedicated to certain types of data, though the number of display fields in each row may vary. For example, as shown, the first row 270 may include arterial flow data, the second row 272 may include venous flow and/or percent line occlusion and pressure data, the third row 274 may include gas flow and blood gas data (e.g., saturation, partial pressures, etc.), and the fourth row 276 may include temperature data. Rows, display fields, functional display areas, and/or the like may be distinguished using any number of different techniques such as, for example, color-coding, certain types of fonts, images, and/or the like.

In embodiments, the dynamic area 252 may be configured to present interactive display elements configured to facilitate user interaction with the GUI such as, for example, dropdown menus, input fields, virtual buttons, virtual levers, virtual sliders, and/or the like. In embodiments, for example, the dynamic area 252 may present one or more interactive display elements configured to enable a user to input values, set limits, configure alarms, and/or the like. In embodiments, the dynamic area 252 may include a notification bar 278 for displaying notifications, a status bar 280 for displaying data associated with the current procedure/operation, such as the current system configuration, the patient surface area, the needed perfusion flow for the patient, and/or the like. The dynamic area 252 may be configured to present notifications, alarms, indications of unusual situations, and/or the like, such as, for example, by providing pop-up display areas, displaying certain colors, and/or the like.

The system area 254 may be configured to present representations of states of aspects of the HLM system. For example, in embodiments, the system area 254 may present general system information like actual date and time, battery status and general controls, like locking the touch-panel, exit the current procedure or access the setting menu, and/or the like. The system area 254 may further include a timer area 282 and a navigation area 284. The timer area 282 may include any number of different timers, clocks, and/or the like, and may include interactive display elements configured to enable a user to interact with the timers/clocks. For example, the timer area 282 may include a number of timers intended to measure/document the duration of the individual phases of the current procedure/operation, and each timer may include a time display 286 and one or more interactive buttons 288 for starting the timer, stopping the timer, pausing the timer, clearing the timer, and/or the like. The navigation area 284 may include one or more interactive display elements 290 configured to facilitate enabling a user to access different menus, establish display configurations, and/or the like. As shown in FIGS. 2C and 2D, the GUI may further include the display regions 216B, 218B, 220B, and 222B.

The illustrative control assembly 200 and GUI 246 shown in FIGS. 2A-2D are not intended to suggest any limitation as to the scope of use or functionality of embodiments of the present disclosure. The illustrative control assembly 200 and GUI 246 also should not be interpreted as having any dependency or requirement related to any single component or combination of components illustrated therein. For example, in embodiments, the control assembly 200 may include one or more speakers and/or microphones. Additionally, various components depicted in FIGS. 2A-2D may be, in embodiments, integrated with various ones of the other components depicted therein (and/or components not illustrated), all of which are considered to be within the ambit of the present disclosure.

Figure 3:
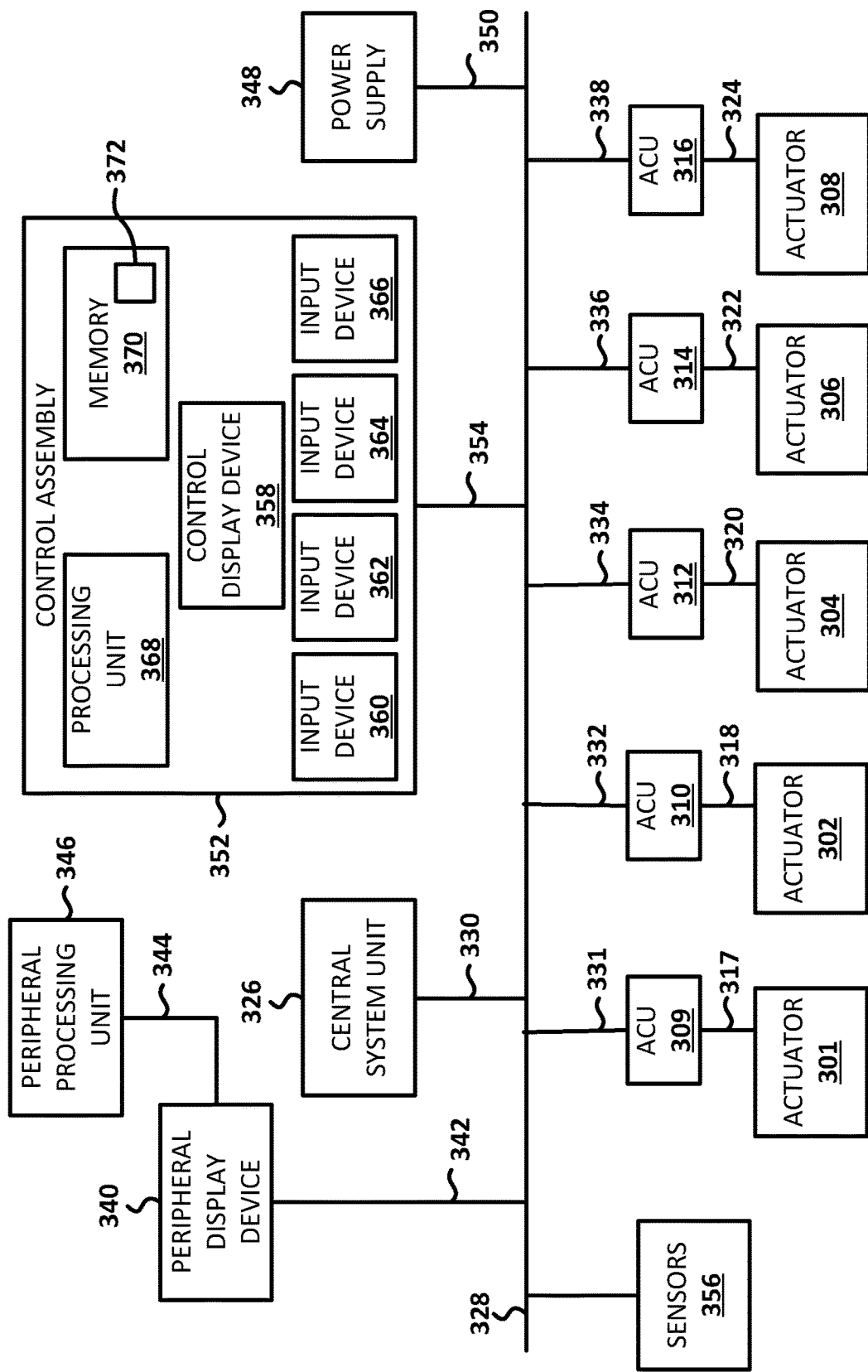
FIG. 3 is a block diagram depicting an illustrative operating environment, in accordance with embodiments of the subject matter disclosed herein.

FIG. 3 is a block diagram depicting an illustrative operating environment in accordance with embodiments of the subject matter disclosed herein. According to embodiments, the illustrative operating environment 300 may be implemented on an HLM or aspects thereof such as, for example, the HLM 100 depicted in FIGS. 1A-1C, the control assembly 200 depicted in FIGS. 2A-2B, and/or the like.

As shown, the operating environment 300 includes a number of actuators 302, 304, 306, and 308. In embodiments, the actuators 301, 302, 304, 306, and 308 may be pump actuators, valve actuators, and/or the like, and may be, be similar to, include, or be included any one or more of the HLM components 116, 118, 120, 122, and 124 depicted in FIGS. 1A-1B. In embodiments, the operating environment 300 includes a number of actuator control units (ACUs) 309, 310, 312, 314, and 316, each of which is operably connected to a corresponding one of the plurality of actuators 301, 301, 304, 306, and 308, respectively, via a communication link 317, 318, 320, 322, and 324, respectively, as shown in FIG. 3. According to embodiments, for example, an ACU may include an adjustable knob and a display configured to display a value of a device parameter adjustable using the knob. The pump ACU may be configured to set and/or adjust a speed or flow rate of the associated pump. Similarly, a line occluder ACU may be configured to set and/or adjust a value of line occlusion, or the free flow corresponding to it.

In embodiments, each of the actuators 301, 302, 304, 306, and 308 may be operably connected to the bus 328 via actuator-bus communication links. In embodiments, as shown in FIG. 3, these connections may not be present. In embodiments, as shown in FIG. 3, each of the ACUs 309 310, 312, 314, and 316 may be configured to be operably connected to the bus 328, via ACU-bus communication links 331, 332, 334, 336, and 338, respectively. That is, for example, while one or more of the actuators 301, 302, 304, 306, and 308 may be functionally coupled to the bus 328, e.g., via the respective ACUs, the actuators 301, 302, 304, 306, and 308 are not directly coupled to the bus 328. In embodiments, for example, one or more of the actuators 301, 302, 304, 306, and 308 may be able to communicate information to the bus 328, but may not be able to be controlled directly via the bus 328. That is, in embodiments, actuators 301, 302, 304, 306, and 308 may be configured to be controlled only through their respective ACUs, and the corresponding input control devices may have communication links only to the ACUs (via the bus), and not directly to the actuators. This arrangement may facilitate, for example, priority of the ACUs over the input control devices.

As is further shown in FIG. 3, the operating environment 300 further includes a peripheral display device 340 configured to present representations of a subset of the set of parameter data received from the actuators 301, 302, 304, 306, and 308, and/or one or more of the ACUs 309, 310, 312, 314, and 316. The peripheral display device 340 may be operably connected, via a communication link 342, to the bus 328. In embodiments, the peripheral display device 340 may additionally, or alternatively, be operably connected, via a communication link 344, to a peripheral processing unit 346, where the peripheral processing unit 346 may be configured to operate the peripheral display device 340, save data inputted to the peripheral display device, and/or the like. The operating environment 300 includes a power supply 348 operably connected to the bus 328 via a communication link 350.

In embodiments, the peripheral processing unit 346 may be implemented as an interface device configured to facilitate operably (or at least communicably) coupling peripheral devices to the HLM such as, for example, the peripheral display device 340, third party medical devices (e.g., pulse oximeters, capnographs, ventilators, etc.), lighting devices, imaging devices, gas blenders, heaters, coolers, and/or the like.

A control assembly 352 is operably connected to the bus 328 via a control communication link 354. In embodiments, the communication link 354 may include a single cable configured to transport control signals, parameter data (e.g., from one or more sensors 356), power, and/or the like. In embodiments, sensors 356 may include, for example, bubble sensors, pressure sensors, flow sensors, level sensors, temperature sensors, blood gas sensors, and/or the like. In embodiments, the control assembly 352 includes a control display device 358 and a plurality of input control devices 360, 362, 364, and 366. In embodiments, the control assembly 352 may include any number of input control devices (e.g., 1, 2, 3, 4, 5, 6, etc.) and the number of input control devices may be less than or equal to the number of ACUs in an actuator enclosure (e.g., the enclosure 136 depicted in FIG. 1C). In embodiments, each of the input control devices 360, 362, 364, and 366 may be operably connected to the bus 328 via the communication link 354. According to embodiments, any number of the various components of the operating environment 300 may have associated therewith a unique identifier. For example, one component may communicate with another component by associating the other component identifier with the communication intended therefor. In this manner, communications between any two or more components of the operating environment may be placed on the bus 328 and recognized by the intended recipient based on the identifier of the intended recipient. In embodiments, one component may communicate with another component by associating the individual identification of the component transmitting the information accompanied with the identification of the individual type of information transmitted. The intended recipient may be programmed in a way, that allows the intended recipient to filter out the information based on the identification associated with the information.

According to embodiments, the control display device 358 may be configured to display representations of a subset of the set of parameter data received. For example, the control display device 358 may be configured to display a first subset of the set of parameter data, while the peripheral display device 340 may be configured to display a second subset of the set of parameter data, where the first and second subsets may not be equal. In this manner, for example, embodiments of the control display device 358 may be configured to present only specified parameters to the user such as, for example, all of the important parameters for a certain procedure, while parameters of somewhat less importance may be presented by the peripheral display device 340.

In embodiments, the control assembly 352 may include a processing unit 368 and a memory 370. The processing unit 370 may, for example, be configured to control the control display device by, for example, providing the parameters to display, providing the defining a layout of display elements, process user input, and/or the like. The processing unit 368 may include, for example, one or more processors configured to execute computer-executable instructions 372 stored in the memory 370 to cause the processing unit 368 to perform one or more functions such as, for example, to assign one or more of the input control devices 360, 362, 364, and 366 to one or more actuators 302, 304, 306, and 308, one or more ACUs 310, 312, 314, and 316, and/or the like. Note that, in embodiments, one or more ACUs 309 and/or actuators 301 may not be operably connected to an input control device 360, 362, 364, and 366.

In embodiments, each of the input control devices 360, 362, 364, and 366 may be assignable to one or more other components of the operating environment 300 that can be configured to be controlled by an input control device. In embodiments, each of the communication links between the input control devices and the respective actuators, via the corresponding ACUs, may be optional with respect to a respective communication link between the actuator and its corresponding ACU such that each of the input control devices is capable of controlling its corresponding actuator via the corresponding ACU (but having no priority over the ACU—that is, e.g., the ACU prevails over the input control device such that an input entered directly at the ACU may override a command entered at the input control device). In embodiments, each of the input control devices 360, 362, 364, and 366 is operably connected to a corresponding ACU, but is not configured to prevail over the corresponding ACU. In embodiments, one or more of the ACUs may be regarded as emergency ACUs (e.g., those ACUs 138, 140, 142, and 144 that are disposed in the enclosure 136 depicted in FIG. 1C).

In embodiments, for example, the actuator 302 may be controlled by its respective ACU 310 in two ways—either via the communication link 318 or via the respective input control device 360. In embodiments, the ACU 310 may have priority over the input control device 360 in case, for instance, of bus 328 failure, as the actuator 302 can always be controlled by the ACU 310 via communication link 318, but, in that instance, can no longer be controlled by the input control device 360. According to embodiments, as the philosophy of the HLM is to use the ACUs placed in the lower enclosure primarily for emergencies and not for normal operation, the lower ACUs may have priority over the input control devices because they still can control actuators in case the ACUs cannot. In embodiments, in normal operation, causing an input to either an input control device or an ACU may provide the same result on the actuator.

Any one or more of the communication links described herein may be, or include, a wired link, a wireless communication link such as, for example, a short-range radio link, such as Bluetooth, IEEE 802.11, a proprietary protocol, a combination of wired and wireless links, and/or the like. The term "communication link" may refer to a mechanism for communicate some type of information (e.g., control signals, parameter data, etc.) and/or energy (e.g., electrical power) in at least one direction between at least two locations, and should not be understood to be limited to a direct, persistent, or otherwise limited communication channel. That is, according to embodiments, a communication link may be a persistent communication link, an intermittent communication link, an ad-hoc communication link, and/or the like. A communication link may refer to direct communications between components and/or indirect communications that travel between components via at least one other device (e.g., a repeater, router, hub, and/or the like). A communication link may facilitate uni-directional and/or bi-directional communication between components. For example, in embodiments, one or more input control devices 360, 362, 364, and 366 may be configured to communicate, via a wired and/or wireless link, with corresponding ACUs 310, 312, 314, and 316.

According to embodiments, the instructions 372 may be configured to cause the processing unit 368, upon being executed by the processing unit 368, to facilitate presenting a user interface having a number of representations of parameter values, where at least one representation of a parameter value and at least one associated indicator (e.g., an indication of measurement units, an indication of a parameter name, an indication of a parameter, and/or the like) is presented in stacked form. In stacked form, for example, the at least one associated indicator (or at least a portion thereof) overlaps at least a portion of the representation of the parameter value. In this manner, embodiments of the subject matter disclosed herein may facilitate saving display screen space, thereby facilitating providing a more condensed display device that is still capable of presenting the relevant parameters and/or other information to the user as the user operates the machine.

According to embodiments, the parameter value may be rendered using a first font, and the associated indication may be rendered using a second, different, font. A font may refer to any number of different characteristics of displayed text, symbols, numbers, and/or the like. The characteristics may include, for example, line thickness, color value, brightness, contrast (in relation to other fonts, backgrounds, images, etc.), style, and/or the like. For example, although a number and an associated units indication may both be rendered in a certain selectable typeface font like "Calibri," as the term "font" is used herein, they may have different fonts if the thickness of lines is different, the color is different, the brightness is different, and/or the like.

In embodiments, for example, the first font may include a first line thickness and the second font may include a second line thickness, where the first line thickness is greater than the second line thickness. The first font may have a first color value (which may be defined using any number of different color models), the second font may have a second color value, and a background of the user interface may have a third color value, where the first, second, and third color values are different. In embodiments, for example, the second color value may be a color value between the first and third color values, the third color value may be a color value between the first and second color values, or the first color value may be a color value between the second and third color values.

In embodiments, the first font may have a first brightness value, the second font may have a second brightness value, and the background may have a third brightness value. Brightness may be defined in any number of different ways and may, in embodiments, refer to pixel intensity, a color characteristic, and/or the like. In embodiments, for example, the second brightness value may be less than the first brightness value and greater than the third brightness value. According to embodiments, a contrast between the user interface background and the representation of the parameter value may have a first contrast level and a first contrast direction; and a contrast between the associated indication and the representation of the parameter value may have the first contrast level and a second contrast direction. In embodiments, the contrast levels may be different. In embodiments, contrast may be defined in any number of ways, such as by a difference between color values and/or brightness values. According to embodiments, the characteristics of the font used to render a parameter value are selected and/or configured such that the parameter value is visible from a distance, and the characteristics of the font used to render the associated indication(s) may be selected and/or configured such that the associated indication is only visible to a user that is positioned near the HLM 100.

According to embodiments, any one or more of the components of the illustrative operating environment 300 may be implemented on one or more computing devices. A computing device may include any type of computing device suitable for implementing aspects of embodiments of the disclosed subject matter. Examples of computing devices include specialized computing devices or general-purpose computing devices such "control units," "control assemblies," "workstations," "servers," "hand-held devices," "heart lung machines," "controllers," and the like, all of which are contemplated within the scope of FIG. 3, with reference to various components of the operating environment 300.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wired and/or wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The illustrative operating environment 300 shown in FIG. 3 is not intended to suggest any limitation as to the scope of use or functionality of embodiments of the present disclosure. The illustrative operating environment 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4A:
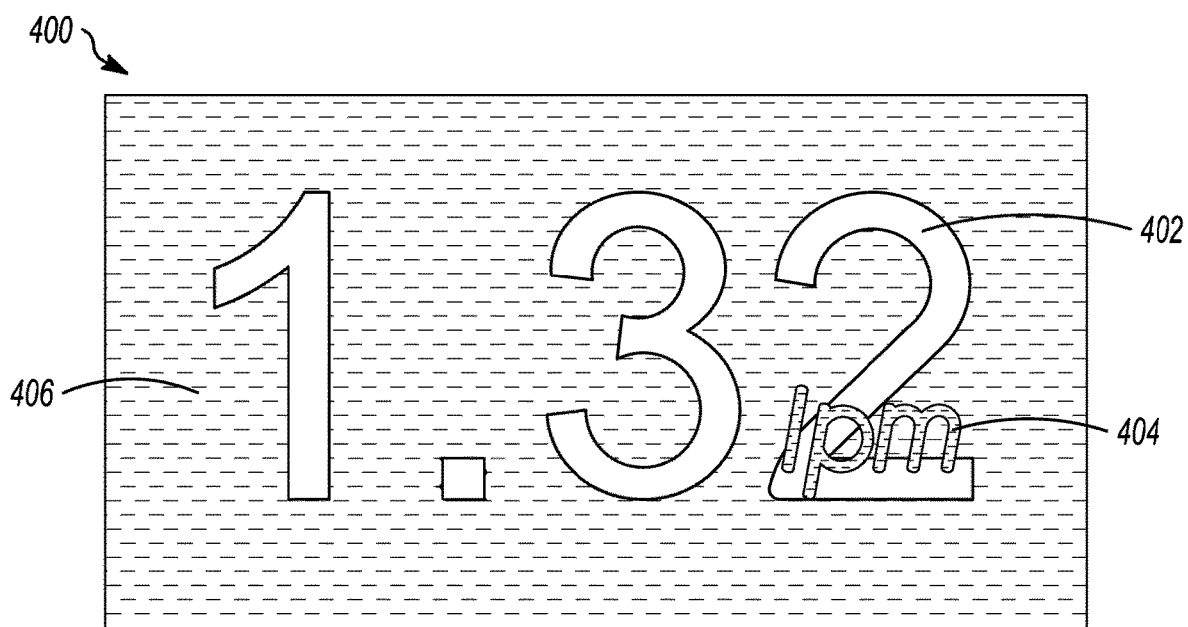
FIG. 4A depicts an illustrative value field of a user interface presenting a representation of a parameter value and an associated indication, in accordance with embodiments of the subject matter disclosed herein.

FIG. 4A depicts an illustrative value field 400 of a user interface presenting a representation 402 of a parameter value and an associated indication 404, in accordance with embodiments of the subject matter disclosed herein. As shown in FIG. 4A, the representation of 402 of the parameter value has a first font and the associated indication 404 has a second font. As shown, for example, the first font (associated with the representation 402 of the parameter value) has a first line thickness and the second font (associated with the associated indication 404) has a second line thickness, wherein the first line thickness is greater than the second line thickness. Additionally, as shown, the first font has a first color value, the second font has a second color value, and the background 406 of the user interface has a third color value, where the first, second, and third color values are different. The first font may also have a first brightness value, the second font may have a second brightness value, and a background of the user interface may have a third brightness value, where the first, second, and third brightness values are different. For example, the second brightness value may be less than the first brightness value and greater than the third brightness value. In embodiments, the various color values and brightness values may be configured such that a contrast between the user interface background 406 and the representation 402 of the parameter value has a first contrast level and a first contrast direction; and a contrast between the associated indication 404 and the representation 402 of the parameter value has a second contrast level and a second contrast direction. In embodiments, the contrast between the associated indication 404 and the representation 402 of the parameter value may have the first contrast level and the second contrast direction. Any number of other font characteristics may be implemented to facilitate making the representation 402 of the parameter value visible at greater distances away from the display device than distances at which the associated indication 404 is visible.

Figure 4B:
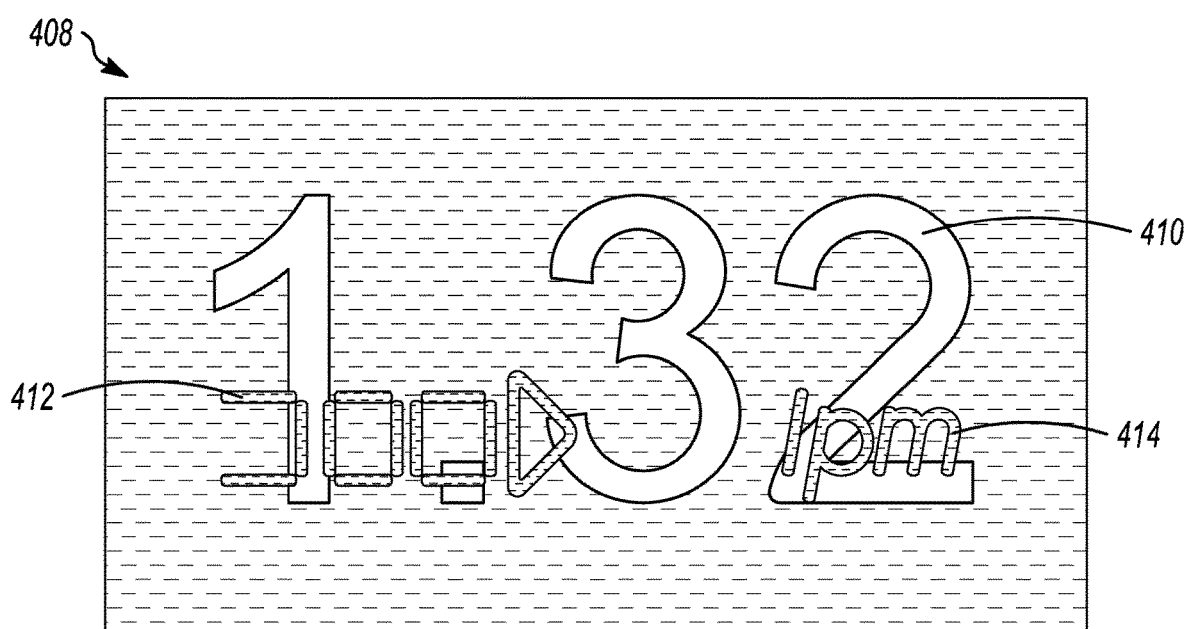
FIG. 4B depicts another illustrative value field of a user interface presenting another representation of a parameter value and two associated indications, in accordance with embodiments of the subject matter disclosed herein.

According to embodiments, as indicated above, the associated indication may include an indication of measurement units, an indication of a type of parameter value, and/or the like. FIG. 4B depicts another illustrative value field 408 of a user interface presenting another representation 410 of a parameter value and two associated indications 412 and 414, in accordance with embodiments of the subject matter disclosed herein. As shown, the associated indication 412 may include a symbol configured to represent a parameter value type and/or name. For example, the associated indication 412 may be configured to indicate that the representation 410 of the parameter value corresponds to arterial flow. The associated indication 414, as shown, may indicate measurement units corresponding to the parameter value. Any number of different symbols may be used as associated indications, in accordance with embodiments of the subject matter disclosed herein.

The illustrative value fields 400 and 408 shown in FIGS. 4A and 4B, respectively, are not intended to suggest any limitation as to the scope of use or functionality of embodiments of the present disclosure. The illustrative value fields 400 and 408 also should not be interpreted as having any dependency or requirement related to any single component or combination of components illustrated therein. Additionally, various components depicted in FIGS. 4A and 4B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A heart lung machine (HLM), comprising:
   a trolley including a base and at least one mast assembly attached to the base;
   a plurality of actuators coupled to the trolley;
   a peripheral processing unit coupled to the trolley and configured to receive a set of parameter data from the plurality of actuators;
   a peripheral display device coupled to the trolley and configured to present a subset of the set of parameter data; and
   a control assembly coupled to the trolley and comprising a control display device configured to present a user interface having a representation of a parameter value displayed as alphanumeric text and an associated indication displayed as alphanumeric text and/or a symbol, wherein at least a portion of the associated indication overlaps at least a portion of the representation of the parameter value.

2. The HLM of claim 1, wherein the representation of the parameter value is rendered using a first font, and wherein the associated indication is rendered using a second, different, font.

3. The HLM of claim 2, wherein the first font has a first line thickness and the second font has a second line thickness, wherein the first line thickness is greater than the second line thickness.

4. The HLM of claim 2, wherein the first font has a first color value, the second font has a second color value, and a background of the user interface has a third color value, wherein the first, second, and third color values are different.

5. The HLM of claim 2, wherein the first font has a first brightness value, the second font has a second brightness value, and a background of the user interface has a third brightness value, wherein the first, second, and third brightness values are different.

6. The HLM of claim 5, wherein the second brightness value is less than the first brightness value and greater than the third brightness value.

7. The HLM of claim 5, wherein a contrast between the user interface background and the representation of the parameter value has a first contrast level and a first contrast direction; and wherein a contrast between the associated indication and the representation of the parameter value has the first contrast level and a second contrast direction.

8. The HLM of claim 1, wherein the associated indication comprises an indication of measurement units.

9. The HLM of claim 1, wherein the associated indication comprises an indication of a parameter name.

10. One or more non-transitory computer-readable media having embodied thereon computer-executable instructions that, when executed by a processing unit, cause the processing unit to:
   facilitate presenting a user interface on a control display device of a heart lung machine, the user interface simultaneously displaying:
      a representation of a parameter value displayed as alphanumeric text in a first location on the control display device; and
      an associated indication displayed as alphanumeric text and/or a symbol, wherein at least a portion of the associated indication is displayed at a second location on the control display device that overlaps at least a portion of the representation of the parameter value at the first location;
   wherein the representation of the parameter value and the associated indication are readable simultaneously.

11. The media of claim 10, wherein the representation of the parameter value is rendered using a first font, and wherein the associated indication is rendered using a second, different, font.

12. The media of claim 11, wherein the first font has a first line thickness and the second font has a second line thickness, wherein the first line thickness is greater than the second line thickness.

13. The media of claim 11, wherein the first font has a first color value, the second font has a second color value, and a background of the user interface has a third color value, wherein the first, second, and third color values are different.

14. The media of claim 11, wherein the first font has a first brightness value, the second font has a second brightness value, and a background of the user interface has a third brightness value, wherein the first, second, and third brightness values are different.

15. The media of claim 14, wherein the second brightness value is less than the first brightness value and greater than the third brightness value.

16. The media of claim 14, wherein a contrast between the user interface background and the representation of the parameter value has a first contrast level and a first contrast direction; and wherein a contrast between the associated indication and the representation of the parameter value has the first contrast level and a second contrast direction.

17. The media of claim 10, wherein the associated indication comprises an indication of measurement units.

18. The media of claim 10, wherein the associated indication comprises an indication of a parameter name.

19. A method of presenting a user interface on a control display device of a heart lung machine (HLM), the HLM comprising a plurality of actuators; a peripheral processing unit configured to receive a set of parameter data from the plurality of actuators; a peripheral display device configured to present a subset of the set of parameter data; and a control assembly comprising the control display device, the method comprising:
   displaying a representation of a parameter value displayed as alphanumeric text on the control display device; and
   displaying an associated indication displayed as alphanumeric text and/or a symbol on the control display device, wherein at least a portion of the associated indication overlaps at least a portion of the representation of the parameter value, wherein the representation of the parameter value and the associated indication are readable simultaneously.

20. The method of claim 19, further comprising:
   rendering the representation of the parameter value using a first font having a first line thickness; and
   rendering the associated indication using a second, different, font having a second line thickness that is less than the first line thickness, the first font having a first brightness value, the second font having a second brightness value, and a background of the user interface having a third brightness value, wherein the second brightness value is less than the first brightness value and greater than the third brightness value.

\* \* \* \* \*